(12) United States Patent
Herron

(10) Patent No.: US 6,959,246 B2
(45) Date of Patent: Oct. 25, 2005

(54) CARBONATE PERMEABILITY

(75) Inventor: Michael M. Herron, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 99 days.

(21) Appl. No.: 10/747,424

(22) Filed: Dec. 29, 2003

(65) Prior Publication Data

US 2005/0148080 A1 Jul. 7, 2005

(51) Int. Cl.$^7$ .............................................. G01V 3/00
(52) U.S. Cl. ....................................... 702/12; 324/303
(58) Field of Search ............................ 702/6, 8, 7, 11, 702/12, 13; 324/303; 703/10; 73/152.05, 73/152.06

(56) References Cited

U.S. PATENT DOCUMENTS

| | | | |
|---|---|---|---|
| 6,047,595 A | 4/2000 | Herron et al. | 73/152.05 |
| 6,140,816 A | 10/2000 | Herron | 324/303 |
| 6,571,619 B2 | 6/2003 | Herron et al. | 73/152.14 |
| 6,691,037 B1 * | 2/2004 | Poe et al. | 702/13 |
| 6,714,871 B1 * | 3/2004 | Xu et al. | 702/12 |
| 6,833,699 B2 * | 12/2004 | Galford et al. | 324/303 |
| 2003/0231017 A1 * | 12/2003 | Kiesl et al. | 324/303 |

OTHER PUBLICATIONS

Ahmed, U. et al. *Permeability Estimation: The Various Sources and Their Interrelationships.* SPE 19604 (May 1991).
Coates, G. R. et al. *The MRIL in Conoco 33-1—An Investigation of a New Magnetic Resonance Imaging Log.* Trans. SPWLA 32nd Ann. Log. Symp., New Orleans, LA, Paper DD (1991).
Timur, A. *Producible Porosity and Permeability of Sandstones Investigated Through Nuclear Magnetic Resonance Principles.* The Log Analyst (Jan-Feb 1969), pp. 3-11.

* cited by examiner

Primary Examiner—Donald McElheny, Jr.
(74) Attorney, Agent, or Firm—Jody Lynn DeStefanis; William B. Batzer; Dale Gaudier

(57) ABSTRACT

A modification to the Coates-Timur relationship to produce a more coherent relationship applicable to carbonate formations is disclosed. In this method, permeability may be determined using porosity and the ratio of bound fluid volume to (1—bound fluid volume). This method also allows for improved estimation of irreducible water saturation of a carbonate formation using the ratio of $k^c$ and $(e\phi^f + k^c)$. Likewise, the bound fluid volume of a carbonate formation may be determined using the ratio of $\phi k^c$ and $(e\phi^f + k^c)$. In these relationships, e, x, and f are constants according to the following relationships $e=x^c$, $f=bc+1$, x is between 1 and 100 mD (preferably 10 mD).

19 Claims, 4 Drawing Sheets

CARBONATE PERMEABILITY

FIELD OF THE INVENTION

The present invention relates to a method for determining characteristics of carbonate formations and, more particularly, to a method for determining the permeability or bound fluid volume of carbonate formations.

BACKGROUND OF THE INVENTION

Estimating permeability of sedimentary formations is one of the most important factors in distinguishing economic from uneconomic reservoirs. Generally, however, the estimation of permeability from log data has been only partially successful. The Coates-Timur relationship is widely used in magnetic resonance well logging to correlate permeability to two parameters, porosity ($\phi$) and bound fluid volume (BFV) as follows:

$$k = a\phi^b \left( \frac{\phi - BFV}{BFV} \right)^c \qquad (1)$$

where a, b, and c are empirical constants with common values of 10000, 4, and 2. BFV is the product of porosity and irreducible water saturation, $S_{wirr}$, so the equation above can also be given as:

$$k = a\phi^b \left( \frac{1 - S_{wirr}}{S_{wirr}} \right)^c \qquad (2)$$

Using the default values of a, b, and c, this can be rearranged to:

$$S_{wirr} = \frac{100\phi^2}{100\phi^2 + \sqrt{k}} \qquad (3)$$

Substantially more detailed discussions regarding the Coates-Timur equation can be found in:

Timur, A., 1969, "Producible porosity and permeability of sandstones investigated through NMR principles," *Log Analyst*, 10(1), 3–11;

Ahmed, U., Crary, S. F. and Coates, G. R., 1989, "Permeability estimation: the various sources and their interrelationship," SPE 19604; and Coates, G. R., Miller, M., Gillen, M. and Henderson, G., 1991, "The MRIL in Conoco 33-1—an investigation of a new magnetic resonance imaging log," Trans. SPWLA 32th Ann. Log. Symp., New Orleans, La., Paper DD.

Each of these references are incorporated by reference herein in their entireties.

However, the Coates-Timur relationship between porosity, irreducible water saturation and permeability often does not adequately describe carbonate formations, which account for approximately 60% of the earth's hydrocarbon reserves.

Accordingly, it is one object of the present invention to present a method of correlating porosity, bound fluid volume, and permeability for most types of carbonate rocks.

SUMMARY OF THE INVENTION

The present invention discloses a modification to the Coates-Timur relationship to produce an improved relationship to determine permeability of carbonate formations, in particular water-wet carbonate formations. Accordingly, the present invention relates permeability to porosity and the ratio of bound fluid volume to (1—bound fluid volume).

In a first embodiment, a method to determine the permeability of a carbonate formation is disclosed comprising: (a) obtaining core data representative of the carbonate formation; (b) determining the porosity and either irreducible water saturation or bound fluid volume of the carbonate formation from the data; (c) estimating the permeability from porosity and the ratio of bound fluid volume to (1—bound fluid volume). Because irreducible water saturation ($S_{wirr}$) generally equals bound fluid volume divided by porosity ($\phi$), the ratio of bound fluid volume to (1—bound fluid volume) can be substituted with the ratio of $S_{wirr}(\phi)$ to (1—$S_{wirr}(\phi)$).

Preferably, the following relationship between permeability, porosity, and bound fluid volume is used:

$$k = x\phi^b \left( \frac{1 - BFV}{BFV} \right)^c,$$

where k is permeability, $\phi$ is porosity, BFV is bound fluid volume and x, b, and c are constants. The data may be nuclear magnetic relaxation time data. Likewise, the porosity of the formation is determined using data develop using pulsed neutron techniques as known in the art. Constants b and c are determined based on the acquired data and x is between 1 and 100 mD, and preferably 10 mD.

In a second embodiment, irreducible water saturation of a carbonate formation may be determined, comprising: (a) obtaining data representative of the carbonate formation; (b) determining the porosity ($\phi$) and permeability (k) of the carbonate formation from the data; and (c) estimating the irreducible water saturation of the carbonate formation using the ratio of $k^c$ and ($e\phi^f + k^c$), wherein c, e, and f are constants. More particularly, $e = x^c$, $f = bc+1$, x is between 1 and 100 mD (preferably 10 mD), and b and c are determined based on the acquired data.

In a third embodiment, the bound fluid volume of a carbonate formation may be determined, comprising: (a) obtaining data representative of the carbonate formation; (b) determining the porosity ($\phi$) and permeability (k) of the carbonate formation from the data; and (c) estimating the bound fluid volume of the carbonate formation using the ratio of $\phi k^c$ and ($e\phi^f + k^c$), wherein c, e, and f are constants. As above, $e = x^c$, $f = bc+1$, x is between 1 and 100 mD (preferably 10 mD), and b and c are determined based on the acquired data.

Further features and applications of the present invention will become more readily apparent from the figures and detailed description that follows.

DETAILED DESCRIPTION OF THE INVENTION

Figure 1:
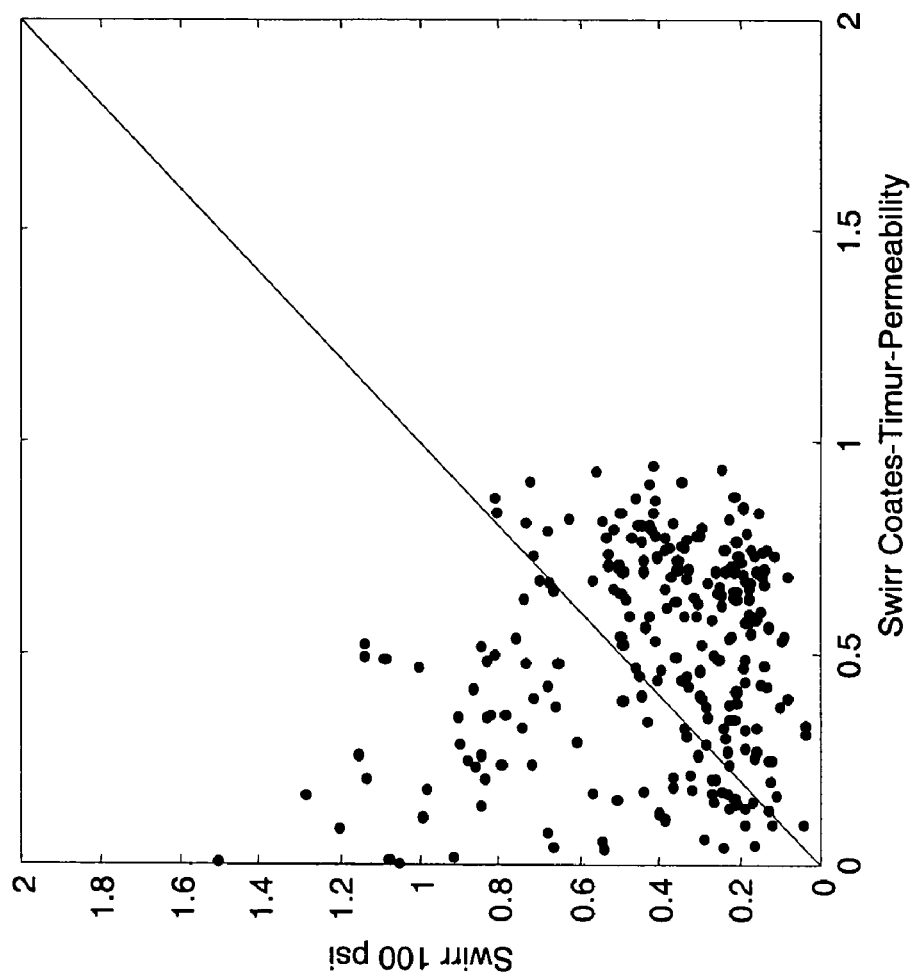
FIG. 1 is a graph depicting predicted $S_{wirr}$ using the Coates-Timur-Permeability equation as compared to measured $S_{wirr}$ (100 psi) values on 208 carbonate samples.

Equation (3) above is known as the Coates-Timur-Permeability equation. A comparison of the Equation (3) to measured $S_{wirr}$ values for carbonate rocks is shown in FIG. 1. The measured $S_{wirr}$ values were obtained by centrifuging 208 carbonate samples at an entry pressure of 100 psi. The ordinate of FIG. 1 is predicted $S_{wirr}$ using Equation (3) and the abscissa is the measured $S_{wirr}$. A 1:1 line is shown for comparison. This figure shows that there is no positive correlation between the predicted $S_{wirr}$ and the measured $S_{wirr}$. For many carbonate samples, particularly low porosity samples, the measured $S_{wirr}$ actually exceeds unity if the measured BFV exceeds a second measure of total porosity. Accordingly, the Coates-Timur relationship between porosity, irreducible water saturation and permeability does not work for many carbonate cores.

Figure 2:
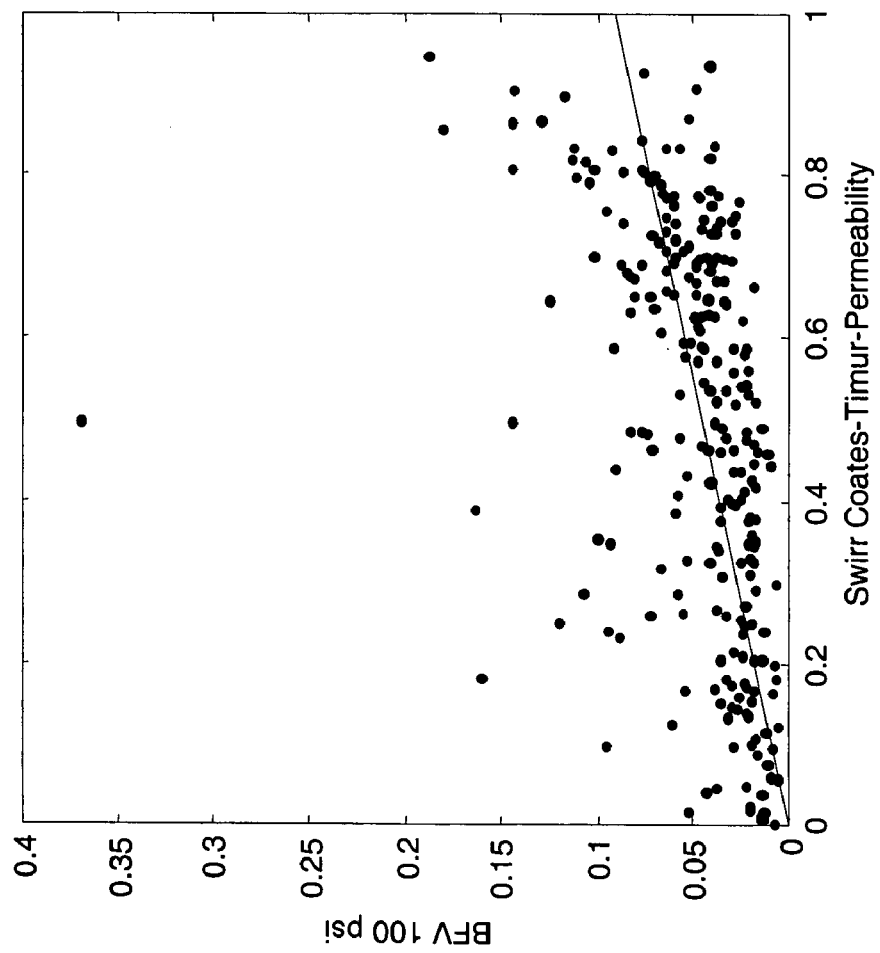
FIG. 2 is a graph depicting predicted $S_{wirr}$ using the Coates-Timur-Permeability equation as compared to measured BFV (100 psi) values on the same 208 samples as FIG. 1.

The predicted $S_{wirr}$ calculated using Equation (3) shows a better correlation with measured BFV than with $S_{wirr}$ (see FIG. 2), implying that $$BFV \propto \frac{100\phi^2}{100\phi^2 + \sqrt{k}} \tag{4}$$

Accordingly, it has been discovered that for carbonates bound fluid volume is proportionally related to porosity and permeability.

Equation (4) therefore can be rearranged to produce a modified Coates-Timur relationship for carbonates in Equation (5) with a new premultiplier x.

$$k = x\phi^b \left(\frac{1-BFV}{BFV}\right)^c \tag{5}$$

A typical value of x will be between 1 and 100 mD, preferably 10 mD, compared to the typical value of 10000 mD in the original Coates-Timur relationship (see Equation (1)).

Figure 3:
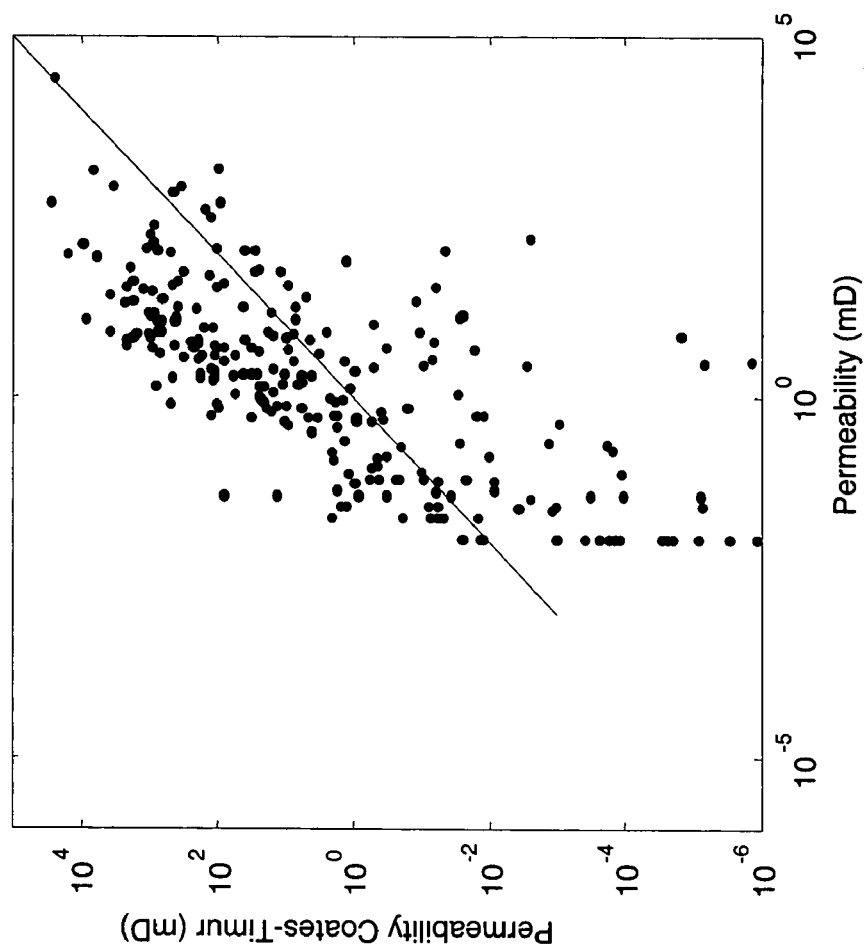
FIG. 3 is a graph depicting the measured permeability on the same 208 samples as FIGS. 1 and 2 as compared to estimates from the Coates-Timur equations using default values of a, b, and c.

FIG. 3 compares measured permeability on 208 carbonate samples with permeability estimated from the Coates-Timur equations using the default values for a, b, and c. The Coates-Timur estimates are generally too high by up to three orders of magnitude.

Figure 4:
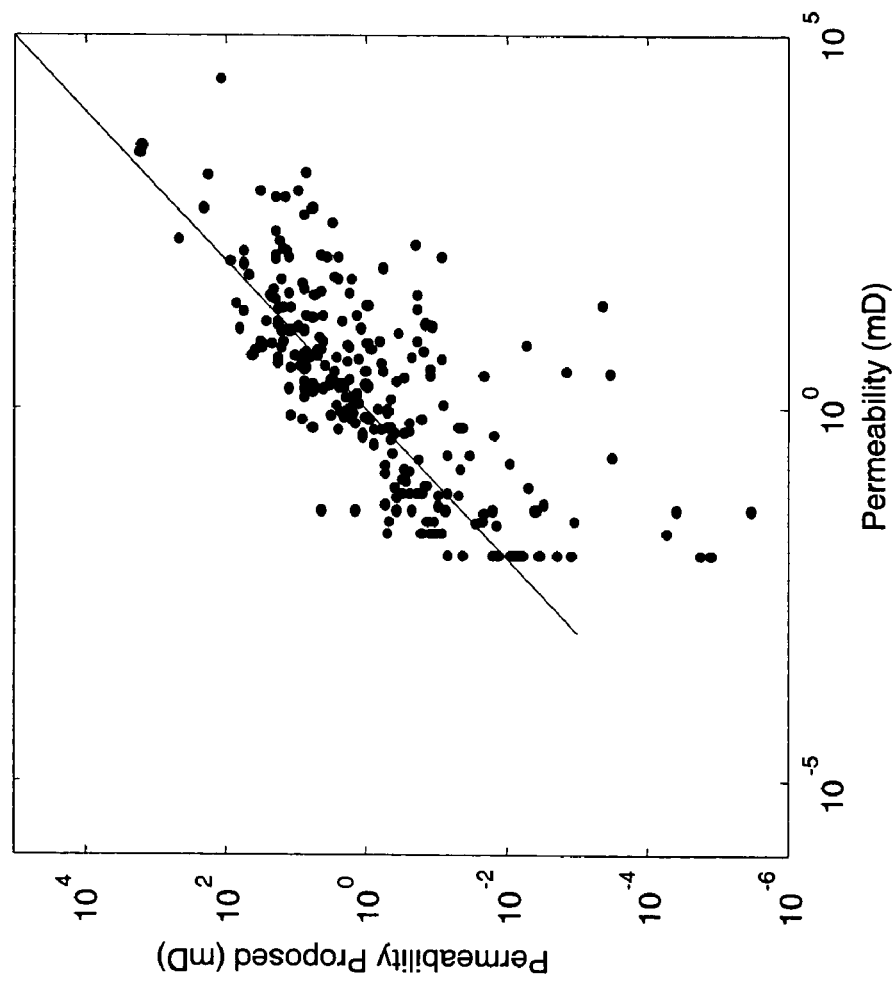
FIG. 4 is a graph depicting the measured permeability on the same 208 carbonate samples as FIGS. 1, 2, and 3 as compared to estimates from Equation (5) using values of x=10 mD, b=4 and c=2.

FIG. 4 shows the same measured permeabilities as FIG. 3 but this time compares them with values derived from Equation (5) using a value of x=10 mD. The estimated permeabilities are in much better agreement with the measured values for most samples. For a few samples, the measured permeabilities are seemingly high, particularly when compared to nearby samples with a similar porosity and composition. In these cases, it is suspected that the measured permeabilities are affected by fractures leading to too high values.

Equation (5) may be rewritten to allow for an improved estimation of irreducible water saturation for carbonate reservoir based on permeability and porosity, as follows:

$$S_{wirr} = \frac{k^c}{(e\phi^f + k^c)} \tag{6}$$

where $e=x^c$, $f=bc+1$, x is between 1 and 100 mD (preferably 10 mD).

Likewise, Equation (5) may be rewritten to allow for an improved estimation of bound fluid volume for carbonate reservoirs based on permeability and porosity, as follows:

$$BFV = \frac{\phi k^c}{(e\phi^f + k^c)} \tag{7}$$

again, where $e=x^c$, $f=bc+1$, x is between 1 and 100 mD (preferably 10 mD).

Accordingly, this new relationship has potential oilfield applications in at least two areas involving carbonate rocks. First, if porosity or bound fluid volume are measured (such as by magnetic resonance logging or pulsed neutron techniques), then this new relationship may be solved to determine an accurate estimate of permeability. Second, if logging measurements can provide estimates of porosity and permeability (such as through k-lambda) then BFV and $S_{wirr}$ can be estimated from this new relationship.

While the invention has been described herein with reference to certain examples and embodiments, it will be evident that various modifications and changes may be made to the embodiments described above without departing from the scope and spirit of the invention as set forth in the claims.

What is claimed is:

1. A method to determine the permeability of a carbonate formation, comprising:
    a. obtaining data representative of said carbonate formation;
    b. determining the porosity ($\phi$) of said carbonate formation from said data and at least one of the group consisting of bound fluid volume (BFV) and irreducible water saturation ($S_{wirr}$) of said carbonate formation from said data; and
    c. estimating the permeability (k) of said carbonate formation using the porosity and the ratio of (1—BFV) and BFV.

2. The method of claim 1, wherein said ratio is the ratio of $(1-S_{wirr}\phi)$ and $S_{wirr}\phi$.

3. The method of claim 1, wherein estimating said permeability based on the following relationship:

$$k = x\phi^b \left(\frac{1-BFV}{BFV}\right)^c$$

wherein x, b, and c are constants.

4. The method of claim 1, wherein the porosity of the formation is determined using data develop using pulsed neutron techniques.

5. The method of claim 1, wherein said data is nuclear magnetic relaxation time data.

6. The method of claim 1, wherein x is between 1 and 100 mD.

7. The method of claim 6, wherein x is 10 mD.

8. A method to determine the irreducible water saturation of a carbonate formation, comprising:
   a. obtaining data representative of said carbonate formation;
   b. determining the porosity ($\phi$) and permeability (k) of said carbonate formation from said data; and
   c. estimating the irreducible water saturation of said carbonate formation using the ratio of $k^c$ and $(e\phi^f+k^c)$, wherein c, e, and f are constants.

9. The method of claim 8, wherein $e=x^c$, $f=bc+1$, wherein b is a constant.

10. The method of claim 9, wherein x is between 1 and 100 mD.

11. The method of claim 10, wherein x is 10 mD.

12. The method of claim 8, wherein the porosity of the formation is determined using data develop using pulsed neutron techniques.

13. The method of claim 8, wherein said data is nuclear magnetic relaxation time data.

14. A method to determine the bound fluid volume of a carbonate formation, comprising:
   a. obtaining data representative of said carbonate formation;
   b. determining the porosity ($\phi$) and permeability (k) of said carbonate formation from said data; and
   c. estimating the bound fluid volume of said carbonate formation using the ratio of $\phi k^c$ and $(e\phi^f+k^c)$, wherein c, e, and f are constants.

15. The method of claim 14, wherein $e=x^c$, $f=bc+1$, wherein b is a constant.

16. The method of claim 15, wherein x is between 1 and 100 mD.

17. The method of claim 16, wherein x is 10 mD.

18. The method of claim 14, wherein the porosity of the formation is determined using data develop using pulsed neutron techniques.

19. The method of claim 14, wherein said data is nuclear magnetic relaxation time data.

* * * * *